United States Patent
Popp et al.

(10) Patent No.: US 7,189,212 B2
(45) Date of Patent: Mar. 13, 2007

(54) ORTHOPEDIC POLYCENTRIC HINGE

(75) Inventors: William J. Popp, Rancho Sante Fe, CA (US); Dennis McKaskle, Escondido, CA (US)

(73) Assignee: Bradley Lineberger, La Habra, CA (US)

( * ) Notice: Subject to any disclaimer, the term of this patent is extended or adjusted under 35 U.S.C. 154(b) by 0 days.

(21) Appl. No.: 11/157,779

(22) Filed: Jun. 21, 2005

(65) Prior Publication Data

US 2006/0287624 A1 Dec. 21, 2006

(51) Int. Cl.
*A61F 5/00* (2006.01)

(52) U.S. Cl. .......................................... 602/16; 602/23

(58) Field of Classification Search .................... 602/5, 602/16, 23, 26, 27, 20; 16/324, 334; 128/882; 403/116, 95; 623/39, 43
See application file for complete search history.

(56) References Cited

U.S. PATENT DOCUMENTS

| 401,933 | A | 4/1889 | DeCamp |
|---|---|---|---|
| 3,817,244 | A | 6/1974 | Taylor |
| 3,901,223 | A | 8/1975 | May |
| 4,372,298 | A | 2/1983 | Lerman |
| 4,493,316 | A | 1/1985 | Reed et al. |
| 4,628,916 | A | 12/1986 | Lerman et al. |
| 4,697,583 | A | 10/1987 | Mason et al. |
| 4,726,361 | A | 2/1988 | Farley |
| 4,732,143 | A | 3/1988 | Kausek et al. |
| 4,777,941 | A | 10/1988 | Borig et al. |
| 5,022,391 | A | 6/1991 | Weidenburner |
| 5,038,763 | A | 8/1991 | Wiggins |
| 5,042,464 | A | 8/1991 | Skwok et al. |
| 5,060,640 | A | 10/1991 | Rasmusson |
| 5,062,858 | A | 11/1991 | Broeck et al. |
| 5,078,127 | A | 1/1992 | Baneman et al. |
| 5,230,696 | A | 7/1993 | Silver et al. |
| 5,292,303 | A | 3/1994 | Bastyr et al. |
| 5,330,418 | A | 7/1994 | Townsend et al. |
| 5,356,370 | A | 10/1994 | Fleming |
| 5,443,444 | A | 8/1995 | Pruyssers |

FOREIGN PATENT DOCUMENTS

| FR | 1187444 | 9/1959 |
|---|---|---|
| GB | 1316572 | 5/1973 |
| GB | 2265087 | 9/1993 |

*Primary Examiner*—Teena Mitchell
*Assistant Examiner*—Shumaya B. Ali
(74) *Attorney, Agent, or Firm*—Greer, Burns & Crain, Ltd

(57) ABSTRACT

A hinge for orthopedic braces includes a pair of support arms, a pair of pivot pins and a hinge plate. The arms are coupled to the hinge plate through the pivot pins and are rotateable between an extension position and a flexion position. The hinge plate has a plurality of adjustment apertures for selective reception of an extension limit pin and a flexion limit pin to selectively restrain rotation of the arms beyond an extension limit and a flexion limit. The pins are retained on the hinge by flexible retainers and are individually positionable among the apertures to adjust the range of motion of the arms. A pair of cover elements pivotally moveable in a plane parallel to the hinge plate provide an open position accommodating access to the pins and a closed position preventing inadvertent displacement of the pins from the apertures.

14 Claims, 2 Drawing Sheets

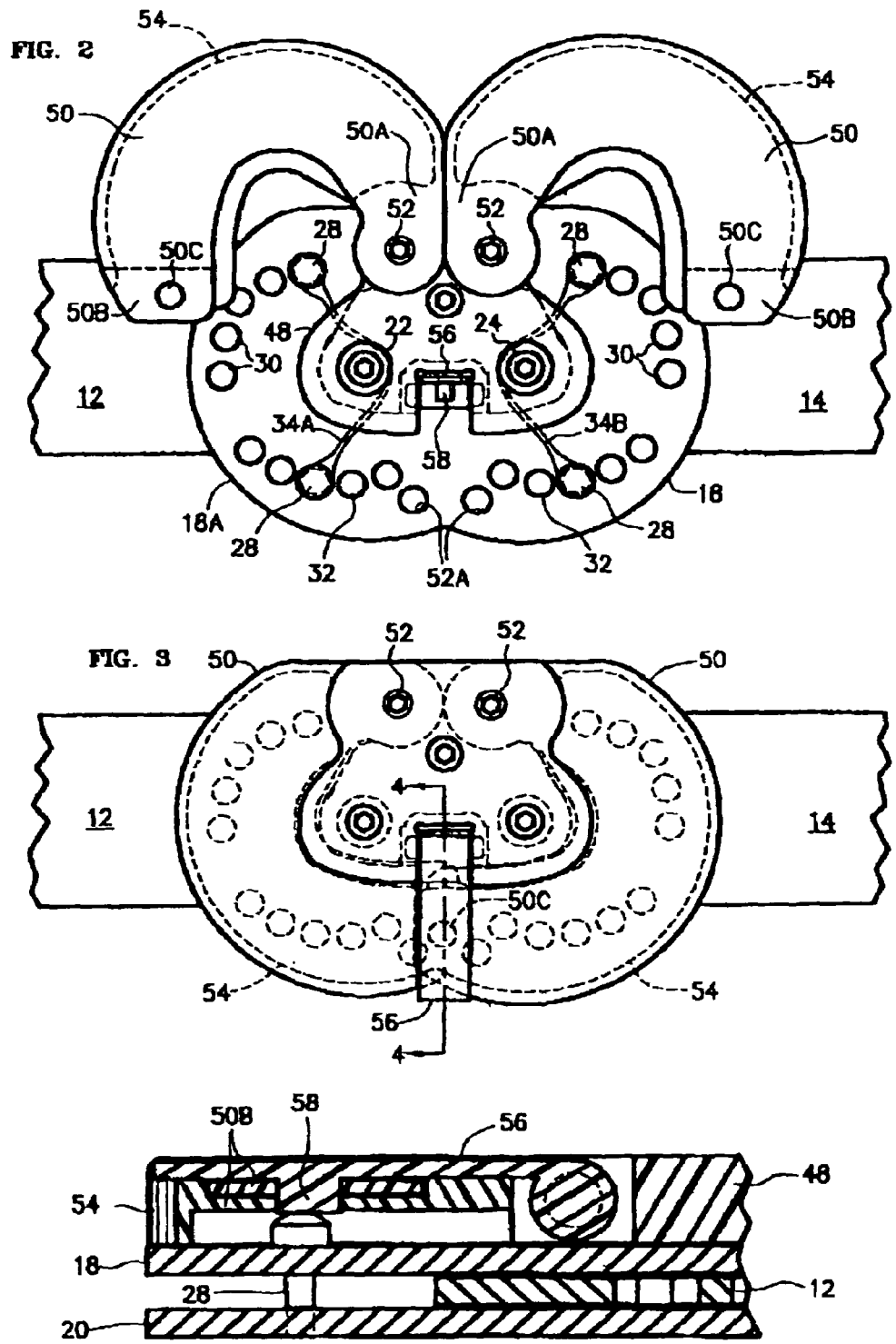

ORTHOPEDIC POLYCENTRIC HINGE

FIELD OF THE INVENTION

The present invention relates to an orthopedic articulating brace, and more particularly, to an orthopedic polycentric hinge for knee braces having rigid relatively moveable support arms and means for conveniently adjusting the range of motion permitted between the arms.

BACKGROUND

The present invention constitutes an improvement on the polycentric hinge disclosed in U.S. Pat. No. 5,443,444, issued Aug. 22, 1995.

As described in said patent, the human knee joint provides for relative articulation of the upper and lower legs, between the femur and tibia, through a plurality of centers or axes over an arc of about 180°. To effectively duplicate the movement of the human knee joint when necessary to mechanically assist the knee, for example, following injury or a surgical procedure, the art has developed articulated knee supporting braces embodying plural axis or polycentric hinges worn about the knee of the patient. These hinges may be used to support the knee joint throughout its full range of motion, or to lock the knee joint in a selected position, or to limit the allowed range of motion of the joint to less than complete extension (straightening) and/or to less than complete flexion (bending) of the knee. During rehabilitation, it is common to initially limit articulation of the knee and to progressively increase the permitted range of motion in gradual increments as healing progresses.

Examples of prior art developments in knee braces may be found in U.S. Pat. Nos. 5,292,303 to Bastyr, et al., U.S. Pat. No. 401,933 to DeCamp, U.S. Pat. No. 5,062,858 to Broeck et al., U.S. Pat. No. 4,732,143 to Kausek et al., U.S. Pat. No. 5,038,763 to Wiggins, U.S. Pat. No. 4,726,361 to Farley, U.S. Pat. No. 4,628,916 to Lerman et al., U.S. Pat. No. 3,817,244 to Taylor, U.S. Pat. No. 3,901,223 to May, U.S. Pat. No. 4,372,298 to Lerman, U.S. Pat. No. 4,493,316 to Reed et al., and British Patent No. 1,316,572 and French Patent No. 1,187,444, among others. Some of these patents disclose knee braces with polycentric hinges and others have hinges with a single axis of rotation.

U.S. Pat. No. 5,443,444 discloses a polycentric hinge for orthopedic knee braces comprising two rigid support arms having cooperating, interlocking, continuously abutting proximal ends rotateably connected to one another by a polycentric hinge assembly including a pair of pivot pins and a hinge plate. Each rigid support arm is rotatably coupled at its proximal end to the hinge plate by a respective one of the pivot pins. The two arms are pivotable about their respective pivot pins along equal arcs of movement between an adjustable extension position and an adjustable flexion position. The total range of motion of the hinge is from substantially complete extension to substantially complete flexion; the rigid arms being positioned in substantially straight line end-to-end relationship in the complete extension position and being positioned in substantially side-by-side relation in the complete flexion position. The hinge accommodates relative angular movement of the rigid support arms substantially between 0° and 180°. The hinge plate is provided with a plurality of adjustment apertures arranged in an angularly spaced apart pattern for reception of a pair of limit pins to intercept rotation along the arc of rotation of at least one of the arms, thereby to limit rotation of both of the arms.

The proximal end portion of the one arm includes an extension facing edge and a flexion facing edge; the extension facing edge being adapted to engage a limit pin in the direction of extension movement and the flexion facing edge being adapted to engage a second limit pin in the direction of flexion movement. The pins, extending through the apertures into which they are inserted, thus restrain movement of the arm beyond the positions defined by the respective limit pins.

Adjustment of the permitted range of motion is obtained by repositioning the pins from one aperture to another to adjust the arc of rotation of the pair of arms, preferably in 15° and/or 30° increments, between a final extension position and a final flexion position. Each of the apertures may be labeled according to a specific angular position for extension or flexion, promoting convenient adjustment.

An openable cover member, specifically a flip-top cap, is provided to allow selected access to the limit pins for purposes of adjustment and to normally overlie the pins and prevent inadvertent or accidental displacement of the pins from their intended positions of adjustment. Also, each of the limit pins is attached to a respective pivot pin by an individual electrometric tether to retain the limit pins against loss or misplacement, while at the same time allowing the limit pins to be appropriately positioned among the apertures.

The flip top cap or cover for the limit pins, unfortunately, is not particularly secure and is prone to popping open, particularly during contact sports, thereby openly exposing the limit pins and permitting the pins to be inadvertently disassociated from their respective apertures, whereupon the hinge is incapable of achieving its intended purpose (unless intended for complete flexion and complete extension). The hinge, until reset, fails its purpose, during which time the knee intended to be protected could suffer further trauma.

SUMMARY OF THE INVENTION

The primary object of the present invention is to provide an improved and essentially fail proof cover for the limit pins for preventing disassociation of the pins from their respective apertures.

A further object of the invention is to provide improved means for retaining the pins in association with the hinge.

In accordance with the present invention, a cover for the limit pins is pivotally or swingably mounted on an axis perpendicular to the hinge plate, rather than on an axis parallel to the hinge plate as with the prior flip-top cap, so that the cover is not prone to being dislodged upon impact in a contact sport or otherwise.

More particularly, in a preferred embodiment of the invention, the cover is comprised of two cover elements swingably mounted on a pivot axis or pivot axes normal to the plane of the hinge plate and moveable toward and away from one another, somewhat like a clam shell, to selectively cover and uncover the limit pins without being prone to inadvertent or accidental uncovering of the pins.

To further secure the cover or cover elements in closed or pin covering position, and to prevent inadvertent or accidental movement of the cover or cover elements to open position, a locking latch is incorporated in the cover assembly.

Additionally, the invention provides improved limit pin retaining means comprising a pair of flexible retainers extending slidably around respective ones of the hinge pins and each carrying at their ends a pair of limit pins.

The present invention thus provides advantageous improvements on the prior art polycentric hinge.

The foregoing and other objects and advantages of the invention will become apparent to those of reasonable skill in the art from the following detailed description, as considered in conjunction with the accompanying drawings.

BRIEF DESCRIPTION OF THE DRAWINGS

FIG. 2 is a top plan view of the hinge showing the cover elements in open or pin uncovering positions;

FIG. 3 is a top plan view of the hinge showing the cover elements in closed or pin covering position; and FIG. 4 is an enlarged fragmentary cross sectional view taken on line 4—4 of FIG. 3 and illustrating the cover elements in closed and latched position.

DETAILED DESCRIPTION

Figure 1:
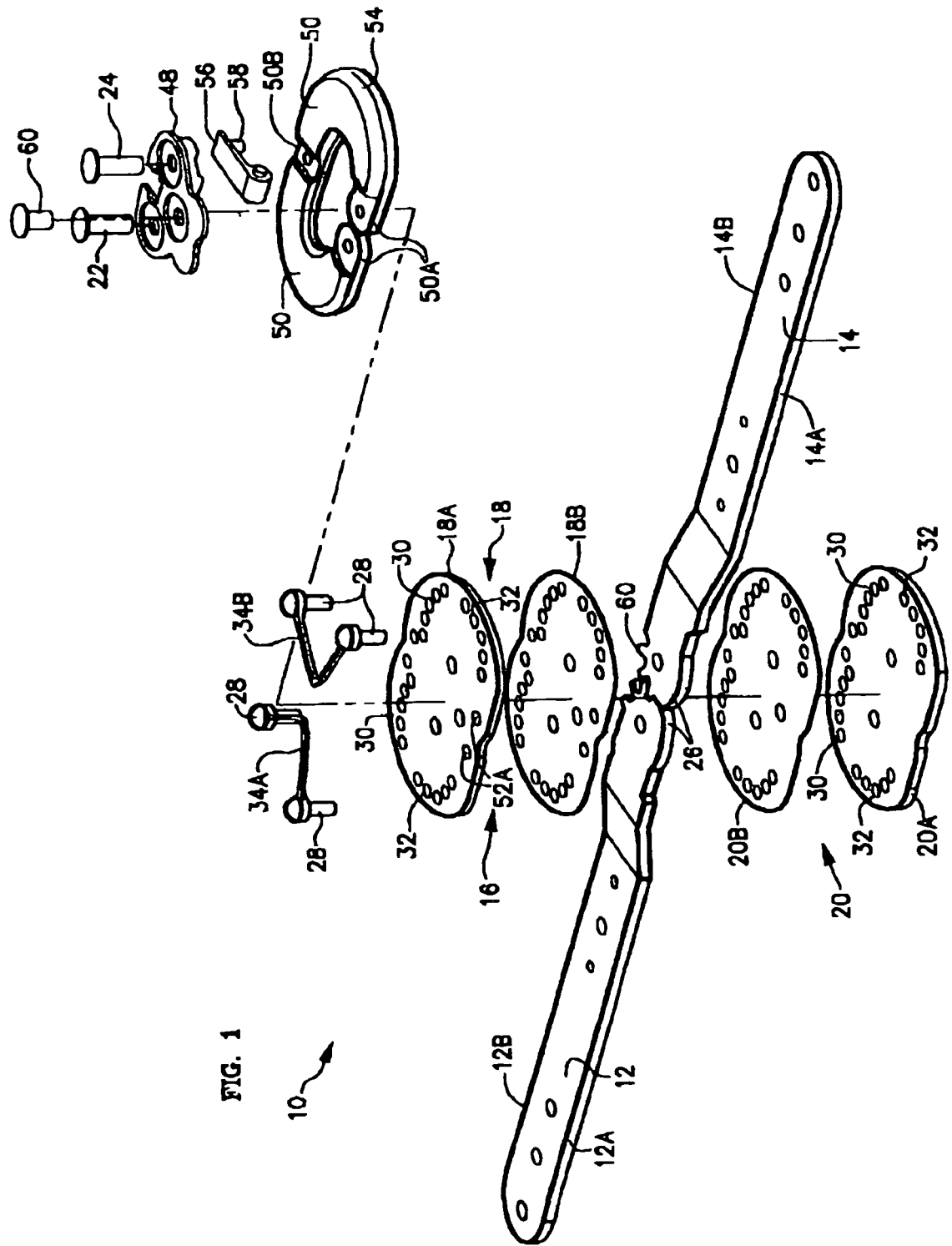
FIG. 1 is an exploded perspective view illustrating the components of the hinge of the invention.

The following is a detailed description of an embodiment of the invention presently contemplated by the inventors to be the best mode of carrying out their invention. Except for the limit pin cover and retainers, the structure of the hinge is essentially the same as that of U.S. Pat. No. 5,443,444, which is incorporated herein by reference and to which reference is made for a more detailed disclosure of the hinge.

Referring to the drawings, an orthopedic polycentric hinge 10 is comprised of a pair of rigid support arms 12, 14 juxtaposed to one another at adjacent or proximal ends and which, in relation to the knee of the patient, have forwardly facing edges 12a, 14a and rearwardly facing edges 12b, 14b. The two support arms 12, 14 are pivotally interconnected at their proximal ends by a hinge assembly 16, comprised preferably of a pair of parallel spaced apart rigid hinge plates 18, 20 overlying the opposite sides, i.e., the exterior and interior sides respectively, of the proximal ends of the support arms 12, 14 and which are pivotally interconnected to the proximal ends of the arms 12, 14. The hinge plates 18, 20 define therebetween a space within which rotation of the arms 12, 14 may occur.

Preferably, the hinge plates 18 and 20 are each comprised of two elements, 18a, 18b and 20a, 20b respectively. The elements 18a, 20a comprise sturdy metal plates providing structural integrity for the hinge and the elements 18b, 20b comprise washers, e.g., sheets of low friction material, such as polytetrafluoroethylene, for minimizing friction between relatively moveable parts and facilitating smooth, low friction movement of the arms 12, 14.

The hinge plates 18, 20 are secured to one another and are pivotally connected to the arms 12, 14 by means of a pair of pivot pins or rivets 22 and 24 respectively. The hinge plates 18, 20 and pivot pins 22, 24 thereby connect the proximal ends of the support arms 12, 14 for relative rotation about a pair of spaced parallel axes in a motion that closely approximates the movement accommodated by the human knee joint.

As illustrated in the drawings, the hinge will be oriented for attachment to the inner or medial side of the right knee and the outer or lateral side of the left knee when the arm 12 is affixed to the upper leg and the arm 14 is affixed to the lower leg, and will be oriented for attachment to the outer or lateral side of the right knee and the inner or medial side of the left knee when the arm 12 is affixed to the lower leg and the arm 14 is affixed to the upper leg. In either orientation, one of the support arms is secured to the upper leg or thigh of the patient above the injured knee and the other support arm is secured to the lower leg or calf below the knee, with the polycentric hinge properly aligned along side the knee. Depending upon the severity of the injury and the degree of support required, the knee may be supported by a single brace on one side of the knee or by a pair of braces located respectively on opposite sides of the knee.

Various means of affixing the support arms to the upper and lower legs of the patient are disclosed in the prior art, for example, U.S. Pat. Nos. 3,786,804, 3,817,244, 4,088,130, 4,361,142, 4,372,298, 4,407,276, 4,493,316 and 4,628,916. To accommodate attachment of the securing means to the brace, a plurality of holes are provided in the arms 12 and 14.

The hinge plates 18, 20 are preferably generally curvilinearly shaped on their side edges along a pair of arcs coincident respectively with the arcs of pivotal movement of the arms 12, 14.

The proximal end surfaces 26 of the two support arms comprise complementary, mutually engaging surfaces formed on arcs of curvature conforming to the polycentric movement between the arms 12, 14, so that the two arms engage one another and derive mutual support and guidance one from the other throughout substantially the entirety of the arc of relative rotation of the arms. Consequently, forces imparted to the hinge 10 in the plane of the hinge are borne by the entirety of the hinge construction, including the abutting surfaces of the support arms, so that the integrity of the hinge 10 is not reliant solely on the hinge plates 18, 20 and pivot pins 22, 24.

Further, to provide for continual interengagement of the components of the hinge for maintaining the same in predetermined engaged relationship with one another, the mutually engaging end surfaces of the arms are provided with gear teeth 60 which are intermeshed and engaged with one another in all positions of relative rotation between the arms.

For injured or injury prone knees that should not be permitted a normal range of movement, protection is provided by a range of motion adjustment means incorporated within the hinge assembly 16. As shown, the hinge plates 18, 20 are provided with aligned pairs of angularly spaced limit stop receiving holes or apertures arranged concentrically about at least one and preferably both of the pivot pins 22 and 24. The limit stop receiving holes are arranged in respective sets 30 for defining extension limit positions and sets 32 for defining flexion limit positions. The holes or apertures are adapted for reception therein of limit pins 28 which in the preferred embodiment are four in number, two for insertion in corresponding pairs of the two sets of extension limit holes 30 and two for insertions in corresponding pairs of the two sets of flexion limit holes 32. While desired limits of extension and flexion could be established by a single set of extension limit holes 30 and a single set of flexion limit holes 32 and the use of just two limit pins 28, the use of four sets of holes and four pins effectively doubles the strength of the motion limiting means, thereby to provide a very sturdy construction having a large number of limit positions without necessitating large or heavy duty limit stop pins and fewer limit positions.

The pins 28 are situated to be engaged in extension by the forward or front edges 12a, 14a of the arms 12, 14 and in flexion by the rearward or rear edges 12b, 14b of the arms 12, 14. The limit pins 28 inserted in corresponding ones of the adjustment apertures 30 thus establish an adjustable range of relative arm rotation for extension, while the limit pins 28 inserted in corresponding ones of the adjustment apertures 32 establish an adjustable range of relative arm rotation for flexion.

Each limit pin is of a size and shape to pass through the selected aperture in hinge plate 18 and to extend into the space between the hinge plates to act as a barrier and limit further rotation of the arms in a given direction, i.e., by engagement therewith of the arms 12, 14. In the preferred embodiment, the limit pins 28 are of a length to extend to and engage within corresponding aligned adjustment apertures provided in and through the hinge plate 20, thereby protecting the limit pins from bending or jamming. The tops of the pins are domed, e.g., semi-spherical, to serve as cam surfaces when pin covers (to be described) are moved to closed position, thereby to fully and firmly seat the pins in the apertures in plates 18 and 20.

By appropriate positioning of the limit or stop pins 28, the hinge can accommodate complete flexion and/or complete extension of the knee, or can selectively limit the knee to one of several degrees of flexion and/or one of several degrees of extension, i.e., a limited range of motion, or the hinge can be locked in any one of several positions of fixed adjustment. Thus, the hinge provides for a protective or rehabilitative knee brace having universal adjustability.

The limit pins 28 are retained in association with the hinge assembly 16 by retainer means 34, specifically a pair of pin retainers 34a, 34b each carrying a pair of the pins 28. Each retainer comprises an elongate, string like central portion slideably extended around a respective one of the pivot pins 22, 24 and enlarged end portions each having an aperture therein for secure reception and retention of a respective one of the pins 28. Preferably, each retainer carries an extension limit pin at one end thereof and a flexion limit pin at the other end thereof. The length and flexibility of the string like central portion facilitates convenient movement of the pins between the adjacent apertures and insertion of the pins into and removal of the pins from the apertures, all without risk of the pins being lost or misplaced.

The limit or stop pins 28 are preferably sized so as to be easily and slideably insertable into and removeable from the adjustment apertures or holes 30, 32. Consequently, once the pins have been inserted into respective motion control or adjustment apertures or holes, it is desirable to provide a cover for the pins so they will not inadvertently become displaced from the selected holes.

In accordance with the invention, one or more cover elements 50 are mounted on the outer surface of the exterior hinge plate 18 for pin covering and uncovering movement in a plane parallel to the plane of the hinge plate. This provides a cover assembly that is resistant to inadvertent displacement of the cover element or elements during use of the hinge, particularly during use of the hinge in a knee brace that is utilized in the course of contact sports. Preferably, the cover element or elements 50 are pivotally or swingably mounted on a pivot pin or pins extending normal, i.e., substantially perpendicular, to the hinge plate so that the element or elements move parallel to the plate.

As shown in the drawings, a preferred embodiment of pin cover is comprised of a base plate 48 and a pair of "clam shell" cover elements 50. The base is mounted on the outer surface of the exterior hinge plate 18 by the pivot pins 22, 24. The base includes, on the interior surface thereof, a pair of spaced parallel pivot pins 52 that extend normal to the plane of the hinge plate 18. Each cover element 50 is generally semi-circular in plan view and has a vertical marginal edge or sidewall 54 for enclosing the heads of the limit pins in the closed positions of the covers. At one pair of ends thereof, the cover elements have end portions 50a of reduced thickness that extend into the interior of the base 48 and are mounted, respectively, on the pivot pins 52. Alternatively, the pivot pins 52 could be provided on the cover element for reception in apertures in the base. In a further and preferred alternative, the end portions 50A of the cover elements have apertures in their upper surfaces for reception of pivot pins 52 on the base 48 and aligned pivot pins on their lower surfaces that are pivotally received in apertures 52A in the upper or exterior hinge plate 18A, thereby to securely mount the cover elements for pivotal movement between the base 48 and the hinge plate 18. In all such structures, the cover elements are swingable toward and away from one another in a plane parallel to the hinge plate between closed and open positions to respectively cover and uncover the limit pins 28 and, in the closed position, to enclose the pins within the side walls 54 of the covers.

At the other pair of ends thereof, the cover elements 50 also have end portions 50b of reduced thickness which in the closed position of the covers are adapted to overlap one another and which, when overlapped, have aligned apertures 50c for reception of a latch pin for securely locking the covers in closed position.

In the preferred embodiment of the invention, the base 48 pivotally mounts a latch member 56 having a latch pin 58 for movement into and out of latching or locking engagement within the aligned apertures 50c at the said other ends 50b of the cover elements. The latch member 56 is pivotally mounted on an axis parallel to the plane of the hinge plate for pivotal movement in a plane normal to the hinge plates. In open or unlatched position, the latch member 56 extends upwardly from the base 48 to an out-of-the-way location to accommodate free access to and adjustment of the limit pins 28. To retain the latch in the open or out-of-the-way location, the base of the latch member is preferably provided with a protrusion or bump that is received within a dimple in the hinge plate 18 to serve as a detent for holding the latch open. In closed and latched position, the latch member is of a length to extend to but not significantly beyond the marginal edges of the cover elements so that it may be manually manipulated with ease but without significant exposure to inadvertent or accidental displacement. Additionally, the latch member fits into a recess formed in the overlapping portions of the cover elements so as to be flush with the outer surfaces of and protected by the cover elements. Also, the latch member at its free end extends between converging curvilinear marginal edges of the cover elements to be further shielded against inadvertent or accidental displacement.

To facilitate assembly of the hinge, the component parts 18A, 48, 50, 56, and 34 (suitably with pins 28 in place) are preferably put together and formed into or a pre-subassembly that is held together by a rivet or similar fastener 60 that extends through aligned apertures in the base 48 and hinge plate 18A. The cover elements 50 are thus pre-assembled for swinging or pivotal movement parallel to the plate 18A. Also, the base 48 is provided in its lower surface with curvilinear grooves for reception of the central portions of the retainers 34 thereby to pre-mount the retainers between the base and the hinge plate for relative sliding movement about the respective pivot pins 22 and 24 to accommodate placement of the limit pins 28 in selected limit pin apertures 30 and 32.

Should any of the limit pins 28 fail to be fully seated in their respective limit apertures, the covers 50 as they are moved to closed position will engage the domed tops of the pins and force them into fully seated positions in the plates 18A and 20A.

The cover elements, when closed and latched, completely enclose the limit pins and are effectively prevented from accidental opening, especially during use in contact sports, and therefore prevent accidental displacement of the limit pins and ensure that the knee brace remains at all times properly adjusted to the particular requirements of the wearer.

The objects and advantages of the invention have thus been shown to be attained in a convenient, practical, economical and facile manner.

While a preferred embodiment of the invention has been herein illustrated and described, it is to be appreciated that various changes, rearrangements and modifications may be made therein without departing from the scope of the invention as defined by the appended claims.

What is claimed is:

1. A having a pair of relatively pivotal arms, a hinge plate mounting said arms for relative pivotal movement and having a plurality of apertures therein, and one or more limit pins insertable in a selected one or selected ones of the apertures for limiting or preventing relative movement of said arms, and
    a cover for said limit pins moveable between an open position and a closed position for permitting access to said pins in open position and for preventing access to said pins in closed position and for preventing accidental displacement of said pins in closed position,
    said cover being movably mounted on the hinge plate for movement in a plane generally parallel to the hinge plate,
    said cover comprised of a pair of cover elements moveably mounted on the hinge plate for movement toward and away from one another between the open and closed positions, each said cover element being mounted for movement in a plane generally parallel to the hinge plate;
    said cover including a base secured to the hinge plate and defining a pair of pivot points generally normal to the hinge plate, said cover elements being pivotally mounted on said base at respective ones of said pivot points for pivotal movement between the open and closed positions;
    said cover elements having portions which overlap each other in the closed position of the cover, and a latch member moveably mounted on said base for movement into locking engagement with the overlapping portions of the cover elements in the closed position and for movement out of engagement with the cover elements to accommodate movement of the cover elements to open position.

2. A hinge as set forth in claim 1, said cover elements at the overlapping portions thereof having inwardly converging curvilinear marginal edges, said latch member extending to said converging edges and being shielded thereby against inadvertent movement out of engagement with said cover elements.

3. A hinge as set forth in claim 1, said cover elements at the overlapping portions thereof defining a recess for reception of the latch member, said latch member when engaged with said overlapping portions lying flush with said cover elements.

4. A hinge as set forth in claim 1, said latch member being pivotally mounted on said base about a pivot axis substantially parallel to said hinge plate for movement in a plane generally normal to said cover elements.

5. A hinge having a pair of relatively pivotal arms, a hinge plate mounting said arms for relative pivotal movement and having a plurality of apertures therein, and one or more limit pins insertable in a selected one or selected ones of the apertures for limiting or preventing relative movement of said arms, and
    a cover for said limit pins moveable between an open position and a closed position for permitting access to said pins in open position and for preventing access to said pins in closed position and for preventing accidental displacement of said pins in closed position,
    said cover being movably mounted on the hinge plate for movement in a plane generally parallel to the hinge plate,
    said hinge plate including two sets of apertures, a pair of limit pins for insertion respectively in the apertures of each set, and a retainer for said limit pins, said retainer comprising an elongate flexible string like central portion and a pair of end portions each carrying a respective one of said pins, said central portion being slideably mounted on said hinge plate and accommodating substantially universal movement of said pins relative to said apertures.

6. A hinge as set forth in claim 5, including a pair of pivot pins pivotally connecting respective ones of the arms to the hinge plate on spaced parallel axes,
    a first set of extension limit apertures in the hinge plate spaced angularly about one of the pivot pins,
    a second set of extension limit apertures in the hinge plate spaced angularly about the other pivot pin,
    a first set of flexion limit apertures in the hinge plate spaced angularly about said one pivot pin,
    a second set of flexion limit apertures in the hinge plate spaced angularly about the other pivot pin,
    a first independently adjustable extension limit pin selectively insertable in the extension limit apertures of the first set of extension limit apertures,
    a second independently adjustable extension limit pin selectively insertable in the extension limit apertures of the second set of extension limit apertures,
    said extension limit pins governing pivotal movement of the arms in extension,
    a first independently adjustable flexion limit pin selectively insertable in the flexion limit apertures of the first set of flexion limit apertures,
    a second independently adjustable flexion limit pin selectively insertable in the flexion limit apertures of the second set of flexion limit apertures,
    said flexion limit pins governing pivotal movement of the arms in flexion,
    a pair of limit pin retainers each having an elongate flexible string like central portion and end portions respectively carrying an extension limit pin and a flexion limit pin,
    the central portion of one of said retainers being slideable about said one pivot pin, extending from said one pivot pin to the first set of extension limit apertures and carrying said first extension limit pin, and extending from said one pivot pin to said first set of flexion limit apertures and carrying said first flexion limit pin,
    the central portion of the other retainer being slideable about said other pivot pin, extending from said other pivot pin to the second set of extension limit apertures and carrying said second extension limit pin, and extending from said other pivot pin to the second set of flexion limit apertures and carrying said second flexion limit pin, said retainers carrying said limit pins so that each limit pin is independently adjustable about the respective pivot pin for selective insertion in the apertures of the respective set of apertures and is retained permanently associated with the respective pivot pin by the respective retainer so as not to be lost or misplaced.

7. A hinge as set forth in claim 6 wherein said retainers accommodate both angular and radial movement of each of the limit pins relative to the pivot pins.

8. A hinge as set forth in claim 6 wherein said cover is of a size and shape conformed substantially to the size and shape of the hinge plate for covering the hinge plate, the limit apertures and the limit pins and for retaining the limit pins in selected apertures, said cover being moveable from a closed position overlying and covering the hinge plate, the limit apertures and the limit pins to an open position where the hinge plate and the limit apertures and the limit pins are exposed to accommodate access to the limit pins and limit apertures.

9. A polycentric hinge for orthopedic braces having a hinge plate, a pair of support arms, and a pair of pivot pins pivotally connecting the support arms to the hinge plate on spaced parallel axes, a first set of extension limit apertures in the hinge plate spaced angularly about one of the pivot pins, a second set of extension limit apertures in the hinge plate spaced angularly about the other pivot pin, a first set of flexion limit apertures in the hinge plate spaced angularly about said one pivot pin, a second set of flexion limit apertures in the hinge plate spaced angularly about said other pivot pin, a first independently adjustable extension limit pin selectively insertable in the extension limit apertures of the first set of extension limit apertures, a second independently adjustable extension limit pin selectively insertable in the extension limit apertures of the second set of extension limit apertures, said extension limit pins governing pivotal movement of the arms in extension, a first independently adjustable flexion limit pin selectively insertable in the flexion limit apertures of the first set of flexion limit apertures, a second independently adjustable flexion limit pin selectively insertably in the flexion limit apertures of the second set of flexion limit apertures, said flexion limit pins governing pivotal movement of the arms in flexion, a pair of limit pin retainers each having an elongate flexible string like central portion and end portions respectively carrying an extension limit pin and a flexion limit pin, the central portion of one of said retainers being slideable about said one pivot pin, extending from said one pivot pin to the first set of extension limit apertures and carrying said first extension limit pin, and extending from said one pivot pin to the first set of flexion limit apertures and carrying said first flexion limit pin, the central portion of the other retainer being slideable about said other pivot pin, extending from said other pivot pin to the second set of extension apertures and carrying said second extension limit pin, and extending from said other pivot pin to the second set of flexion limit apertures and carrying said second flexion limit pin, said retainers carrying said limit pins so that each limit pin is independently adjustable about the respective pivot pin for selective insertion in the apertures of the respective set of apertures and is retained permanently associated with the respective pivot pin by the respective retainer so as not to be lost or misplaced.

10. A hinge as set forth in claim 9 wherein said retainers accommodate both angular and radial movement of each of the limit pins relative to the pivot pins.

11. A hinge as set forth in claim 9 including a cover of a size and shape conformed substantially to the size and shape of the hinge plate for covering the hinge plate, the limit apertures and the limit pins and for retaining the limit pins in selected apertures, said cover being pivotally connected to the hinge plate and moveable from a closed position overlying and covering the hinge plate, the limit apertures and the limit pins to an open position where the hinge plate and all of the limit apertures and all of the limit pins are exposed to accommodate simultaneous access to all of the limit pins and limit apertures.

12. A hinge for an orthopedic brace having a pair of support arms, a hinge plate associated with the arms, at least one pivot pin for connecting the arms for pivotal movement relative to one another, pivotal movement limit apertures in the hinge plate, and a plurality of limit pins selectively insertable in the apertures to govern relative movement of the arms, and including, a pair of cover elements of a size and shape conformed substantial to the size and shape of the hinge plate for covering the hinge plate, the limit apertures and the limit pins and for retaining the limit pins in selected apertures;

said cover elements being pivotally connected to the hinge plate adjacent a marginal edge of the hinge plate and on axes normal to the hinge plate, said cover elements being swingable toward and away from one another between a closed position overlying and covering the hinge plate, the limit apertures and the limit pins and an open position wherein the hinge plate and the limit apertures and the limit pins are exposed to accommodate access to the limit pins and limit apertures.

13. A hinge as set forth in claim 12 including a cover mounting base secured to the hinge plate and extending to a marginal edge of the hinge plate, said cover elements being pivotally mounted on said base adjacent to said marginal edge of and on spaced parallel axes normal to the hinge plate.

14. A hinge as set forth in claim 13 wherein said cover elements include portions that overlap each other in the closed position, said hinge including a latch member pivotally mounted on said base and engageable with the overlapping portions of said cover elements for securely locking said cover elements in the closed position.

* * * * *